United States Patent [19]

Jensen

[11] Patent Number: 4,753,703
[45] Date of Patent: Jun. 28, 1988

[54] METHOD AND APPARATUS FOR FORMING ADHESIVE CONNECTING RINGS AND STACKING SAME ON AN OSTOMY DEVICE

[75] Inventor: Ole R. Jensen, River Vale, N.J.
[73] Assignee: E. R. Squibb & Sons, Princeton, N.J.
[21] Appl. No.: 917,070
[22] Filed: Oct. 8, 1986
[51] Int. Cl.$^4$ .............................................. B32B 31/04
[52] U.S. Cl. ................... 156/256; 156/269; 156/521; 156/568; 414/65; 414/66; 493/343
[58] Field of Search ............ 156/252, 261, 264, 521, 156/568, 256, 269, 516, 517; 493/343, 361, 374; 414/62, 63, 65, 66

[56] References Cited

U.S. PATENT DOCUMENTS

| | | | |
|---|---|---|---|
| 2,438,514 | 3/1948 | Miller | 156/264 |
| 2,618,311 | 11/1952 | Parker | 156/264 |
| 2,805,095 | 9/1957 | Cummings et al. | 414/63 |
| 3,485,693 | 12/1969 | Craven | 156/264 |
| 3,915,785 | 10/1975 | Muller | 156/521 |
| 4,274,623 | 6/1981 | Reist et al. | 414/65 |
| 4,436,470 | 3/1984 | Spletzer et al. | 414/63 |
| 4,701,169 | 10/1987 | Steer | 604/344 |

FOREIGN PATENT DOCUMENTS 2151482  7/1985  United Kingdom .
2153232  8/1985  United Kingdom .
2157567  10/1985  United Kingdom .

Primary Examiner—Frederick R. Schmidt
Assistant Examiner—William E. Terrell
Attorney, Agent, or Firm—James & Franklin

[57] ABSTRACT

Adhesive pouch connecting rings with radially extending gripping portions are formed and stacked in angularly offset relation on a plurality of ostomy faceplates in a highly automated fashion. Sets of rings are die cut from a continuous adhesive coated sheet. Each set includes a plurality of spaced, identically oriented rings, in an arcuate pattern across the sheet. The sheet is intermittently advanced to bring the sets, one at a time, into alignment with faceplates located on a round platform. The platform is indexed to move the faceplates stepwise through a path coincident with the pattern of the ring sets. Each time the platform is indexed, a set of rings is removed from the sheet and the rings are placed on the respective faceplates, each in proper angular relation with the previous rings. Faceplates with a full complement of rings are removed from the platform.

27 Claims, 8 Drawing Sheets

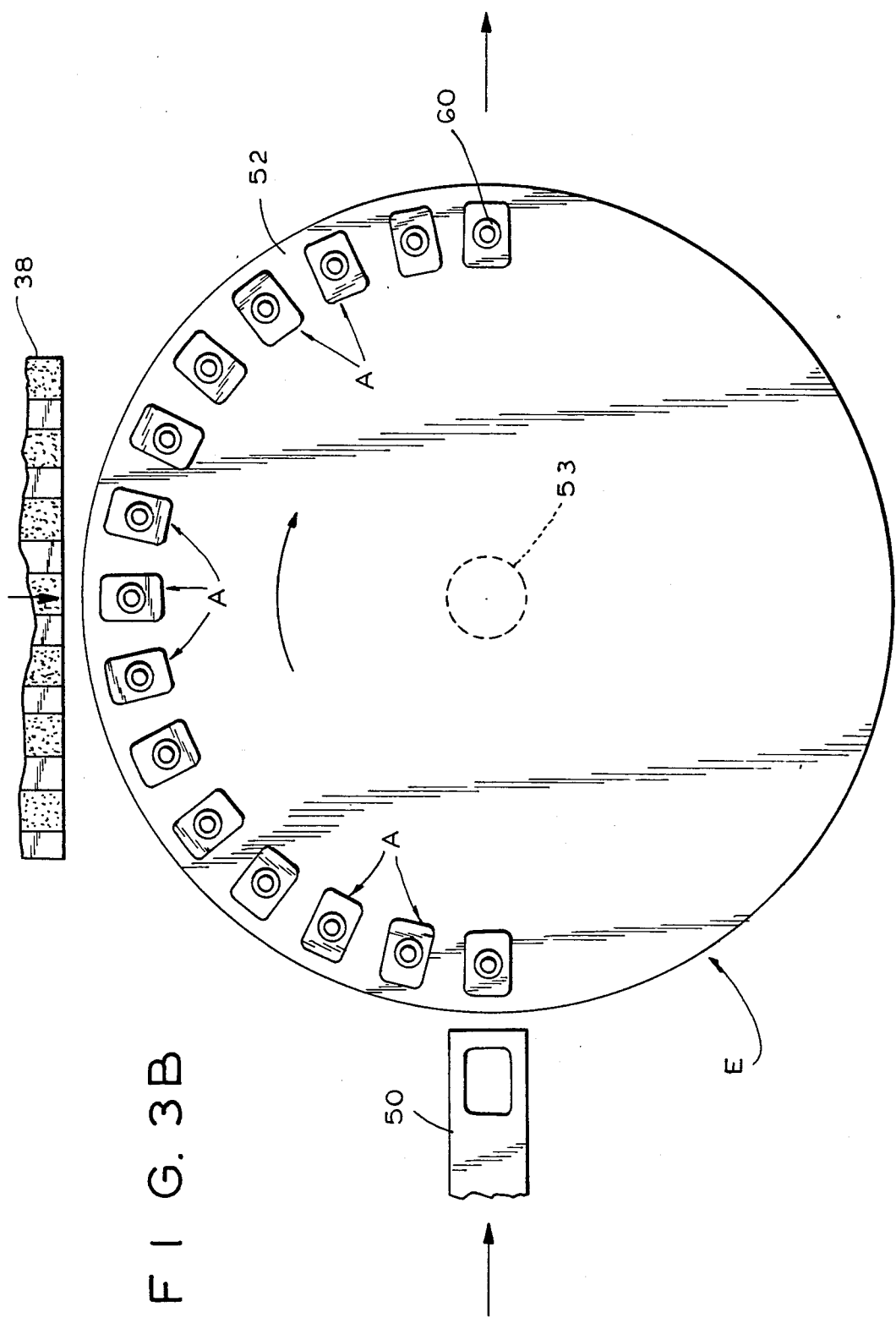

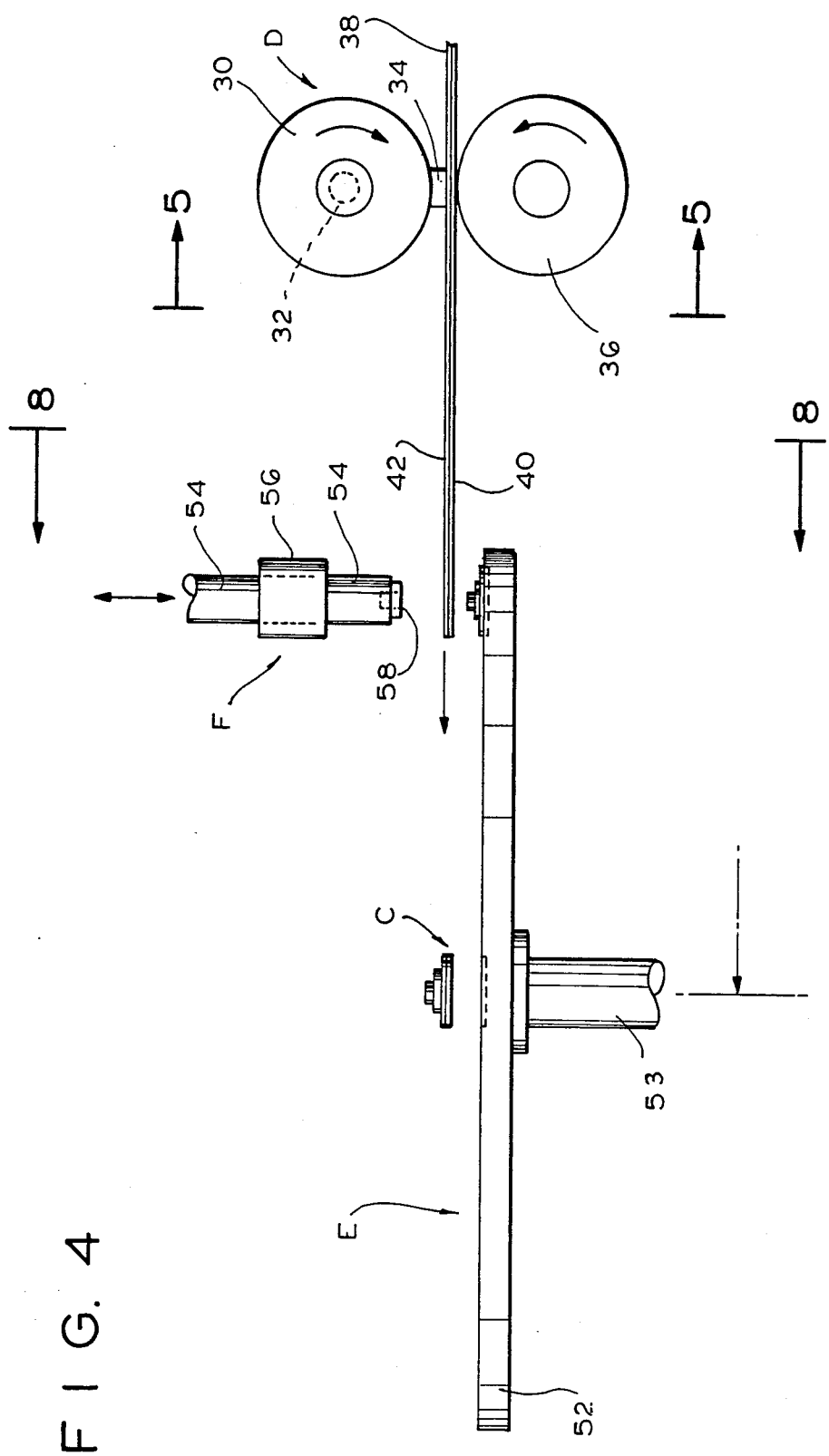

FIG. 5
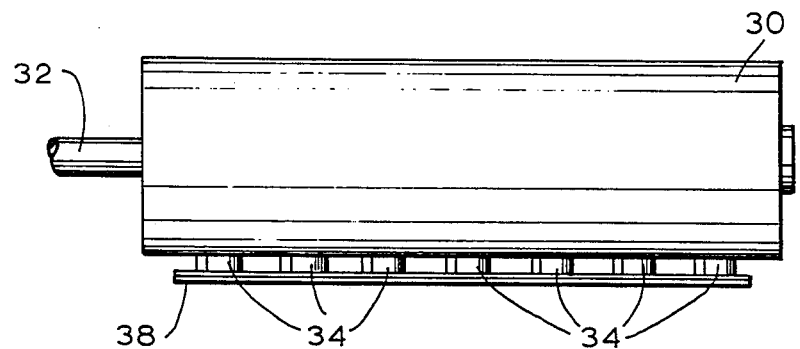
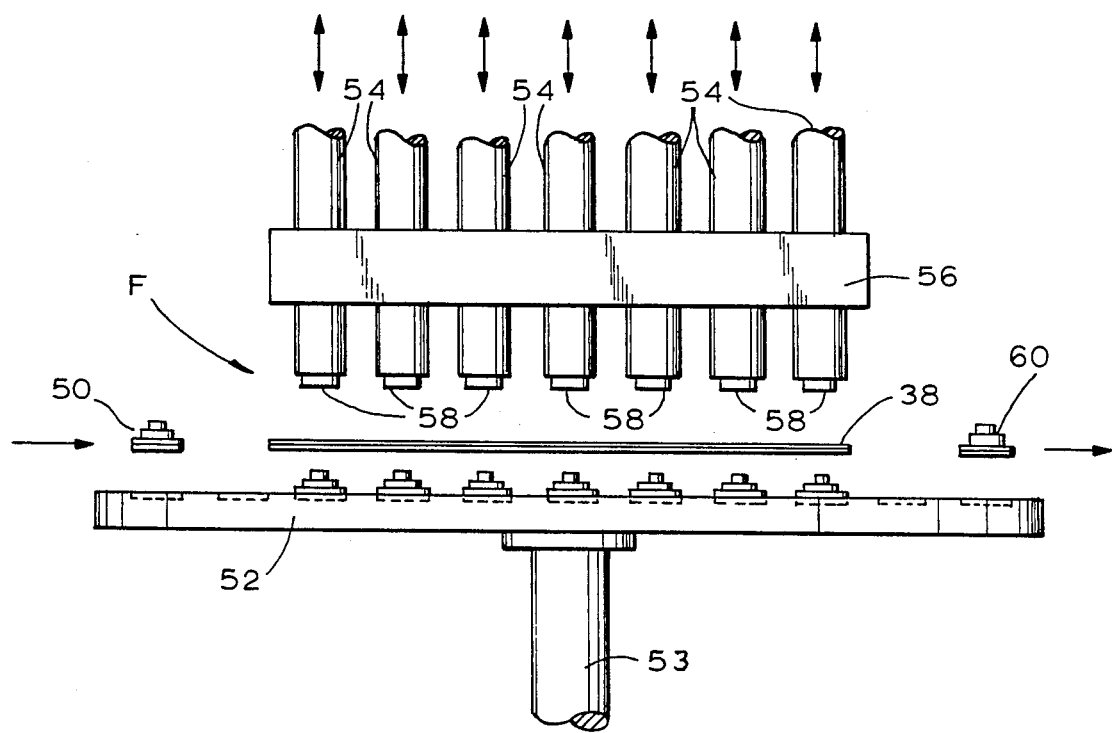
FIG. 8

METHOD AND APPARATUS FOR FORMING ADHESIVE CONNECTING RINGS AND STACKING SAME ON AN OSTOMY DEVICE

The present invention relates to methods and apparatus for the manufacture of ostomy devices and, more particularly, to a method and apparatus for forming adhesive connecting rings and stacking same on faceplates in a highly automated manner.

Conventional ostomy devices include a collection bag or pouch which is attached to a skin-compatible medical grade adhesive pad, also known as a label or faceplate. In some instances, the appliance is designed for a single use and, thus, the faceplate must be removed after a limited time. In other instances, the appliance is designed for multiple use and the pouch or bag can be detached from the adhesive faceplate and emptied or a fresh pouch reattached to the faceplate several times before the faceplate has to be removed from the skin.

Certain single use devices employ an adhesive connecting part affixed to the exterior surface of the faceplate. The connecting part may be provided with a cover layer to protect the adhesive prior to use. The pouch or bag is affixed to the faceplate by removing the cover layer and pressing the pouch or bag against the connecting part. After the pouch or bag has been used, it is removed from the faceplate and cannot be reattached. The faceplate must be removed and replaced by a new faceplate prior to the use of a new pouch or bag.

Because periodic removal of the faceplate may be detrimental and uncomfortable, ostomy devices have been designed for multiple use. Many ostomy devices designed for multiple use utilize a non-adhesive pouch connecting system. In one popular form, relatively rigid plastic interconnecting rings are attached to the faceplate and pouch, respectively. The faceplate and pouch are "snapped" together by exerting the necessary attachment forces on the rings. Since the connecting rings are detachable a large number of times, the pouch can be used repeatedly with the same faceplate. Other types of attachment mechanisms, such as magnetic connection systems and the like, have also been proposed for reusable devices.

However, simple adhesive attachment systems may be preferred in some instances. They are light in weight, perform reliably, are simple to manufacture, and are relatively inexpensive. For these reasons, a simple adhesive attachment system has been developed for a multiple use ostomy device.

In this system, the faceplate is provided with a surface flange to which is mounted a plurality of double-sided adhesive connecting annular parts or rings, each having a cover layer. Each ring is provided with a radially extending gripping portion to permit the user to grip each ring in turn, for removal purposes. The rings are angularly offset such that each of the gripping portions is exposed. The rings can then be peeled off, one at a time.

To mount a pouch to the faceplate, the protective cover layer on the topmost ring is removed, exposing the adhesive surface. The pouch is then pressed against the ring to secure same. After removal of the pouch, the used ring is peeled off and removed. The cover layer for the next ring is peeled off prior to the reattachment of the pouch. The pouch can be repeatedly reattached to the faceplate in this manner by removing each ring in succession until all of the rings have been removed.

Five to seven rings may be provided for each faceplate and, hence, the pouch may be reused five to seven times before the faceplate must be replaced.

In order to produce this type of ostomy appliance, it is necessary that a plurality of annular connecting parts or rings with radially extending gripping portions be formed and mounted on the faceplate in a stack. The parts must be situated in an angularly offset manner such that each radially extending portion is exposed and can be readily grasped by the fingers of the user, such that each ring can be easily removed in turn.

The present invention relates to a method and apparatus for forming such adhesive connecting parts and mounting same on faceplates. The apparatus performs the method in a highly automated manner such that the devices are fabricated in a highly efficient, inexpensive manner.

It is, therefore, a prime object of the present invention to provide a method and apparatus for forming adhesive connecting rings and stacking same on an ostomy device which is highly automated.

It is another object of the present invention to provide a method and apparatus for forming adhesive connecting rings and stacking same on an ostomy device which results in high volume production with low costs per unit.

It is another object of the present invention to provide a method and apparatus for forming adhesive connecting rings and stacking same on an ostomy device which includes reliable operations performable in an economical manner.

In accordance with one aspect of the present invention, apparatus is provided for forming and stacking parts comprising means for forming sets of spaced, substantially identically oriented parts, in a substantially arcuate pattern. A platform is provided, as are means for aligning successive ones of the sets with the platform. Means are provided for rotating the platform such that the operative portion of the platform is moved along a path substantially coincident with the arcuate pattern. Means are provided for distributing the parts from successive aligned sets onto the platform so as to accumulate in angularly offset relation in a plurality of stacks, along the operative portion, as said platform is rotated.

Preferably, the part forming means comprises die cutting means in the form of a rotary die contour cutting roller. The dies are distributed across the surface of the roller in an arcuate pattern. The roller cuts the parts from the sheet, leaving lands or slender connecting bridges which temporarily retain the parts on the sheet. Means are provided for removing the parts by severing the lands.

The parts are formed on a sheet. The sheet preferably includes an adhesive layer. The adhesive layer is separated into spaced sections, preferably strips. The sheet is preferably coated with a protective cover layer.

The aligning means includes means for intermittently advancing the sheet towards the platform. The rotating means rotates the platform in a stepwise fashion. The aligning means advances the sheet towards the platform each time the platform is rotated Means are provided for feeding faceplates, one at a time, to the operative portion of the platform. Means are also provided for removing the faceplates from the operative portion of the platform after the operative portion has moved through the arcuate path.

The parts have a substantially annular configuration. The parts also include a radially extending portion.

In accordance with another aspect of the present invention, a method is provided for forming and stacking parts on a platform. The method comprises the steps of forming spaced, substantially identically oriented parts in an arcuate pattern. Successive ones of the sets are aligned with the platform. The platform is rotated such that the operative part is moved along a path substantially coincident with the pattern of the parts. The parts, in successive aligned sets, are distributed on the platform portion, accumulating in angularly offset relation in stacks, along the platform, as the platform is moved.

The parts are formed by die cutting. The parts are cut from the sheet. leaving thin lands or bridges connecting the part to the sheet. Later, the parts are removed from the sheet by severing the lands.

Part sets are aligned with the platform by intermittently advancing the sheet towards the platform. The platform is rotated in a stepwise fashion. The sheet is advanced toward the platform each time the platform is rotated The faceplates are fed, one at a time, to the operative portion of the platform. The faceplates are removed from the operative portion of the platform after it has moved through the arcuate path.

In accordance with another aspect of the present invention, apparatus is provided for forming annular parts and stacking same The apparatus includes rotary means for cutting spaced sets of the parts on a continuous sheet. Each of the sets includes a plurality of spaced, substantially identically oriented parts in a substantially arcuate pattern across the sheet. A substantially circular platform is provided. Means are provided for advancing the sheet to bring the sets, one at a time, proximate the platform. Means are provided for rotating the platform in stepwise fashion. Means are provided for removing the parts in the proximate set from the sheet, each time the platform is rotated. The removed parts accumulate in a plurality of stacks in angularly offset relation on the platform, as the platform is rotated.

In accordance with another aspect of the present invention, a method is provided for forming annular parts and stacking same on a platform. The method includes the steps of cutting spaced sets of parts on a continuous sheet. Each of the sets comprises a plurality of spaced, substantially identically oriented parts, in a substantially arcuate pattern across the sheet. The sheet is advanced to bring the sets, one at a time, proximate the platform. The platform is rotated in stepwise fashion. The parts in the then proximate set are removed from the sheet each time the platform is rotated. The removed parts accumulate in a plurality of stacks in angularly offset relation on the platform, as the platform is rotated.

In accordance with another aspect of the present invention, apparatus is provided for forming adhesive coated rings with radially extending portions and for stacking same on faceplates. The apparatus comprises means for forming spaced sets of rings on a continuous adhesive coated sheet. Each of the sets comprises a plurality of spaced, substantially identically oriented rings in a substantially arcuate pattern. A rotatable platform is provided. Means are provided for intermittently advancing the sheet to bring the ring sets, one at a time, proximate the platform. Means are provided for feeding faceplates, one at a time, to the platform. Means are provided for indexing the platform to move the faceplates stepwise through a path substantially coincident with the arcuate pattern of the proximate ring set. Means are provided for distributing the rings in the proximate set from the sheet to the faceplate, each time the platform is indexed. The removed rings accumulate on the faceplates in angularly offset relation as the platform is rotated. Means are provided for removing the faceplates from the platform after same have been moved through the arcuate path.

In accordance with another aspect of the present invention, a method is provided for forming adhesive coated rings and for stacking same on faceplates on a platform. The method comprises the step of forming spaced sets of rings on a continuous adhesive coated sheet. Each of the sets comprises a plurality of spaced, substantially identically oriented rings, situated in a substantially arcuate pattern. The sheet is intermittently advanced to bring the sets, one at a time, proximate a rotatable platform. Faceplates are fed, one at a time, to the platform. The platform is indexed to move the faceplates stepwise through a path substantially coincident with the arcuate pattern of the proximate ring set. The rings in the proximate set are removed from the sheet, each time the platform is indexed. The removed parts accumulate on the faceplates in angularly offset relation, as the platform is moved. The faceplates are removed from the platform after same have been moved through the arcuate path.

To these and to such other objects which may hereinafter appear, the present invention relates to a method and apparatus for forming adhesive connecting rings and stacking same on an ostomy device, as set forth in the following specification and recited in the annexed claims, taken together with the accompanying drawings, wherein like numerals refer to like parts, and in which:

Figure 3A:
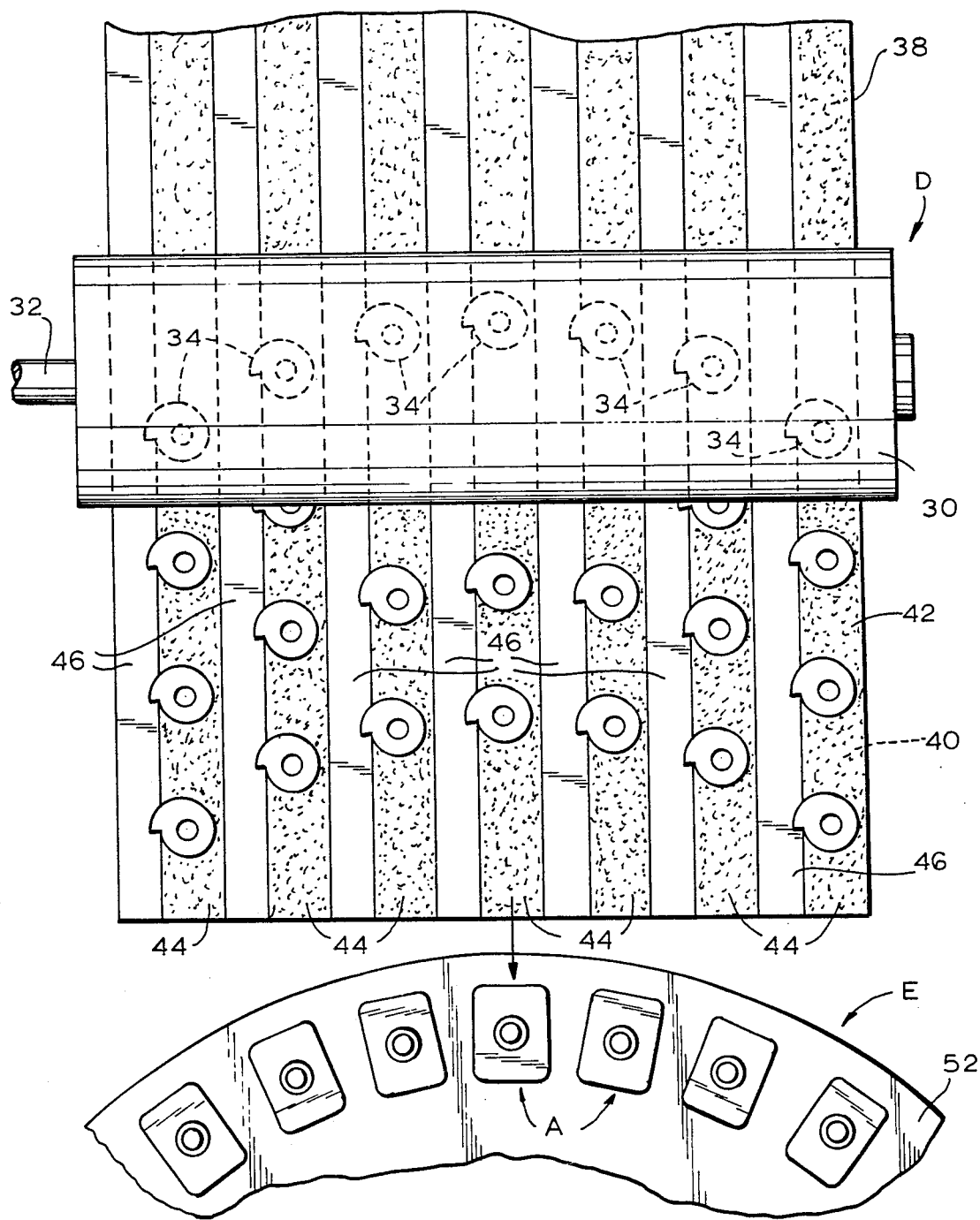
Figure 6:
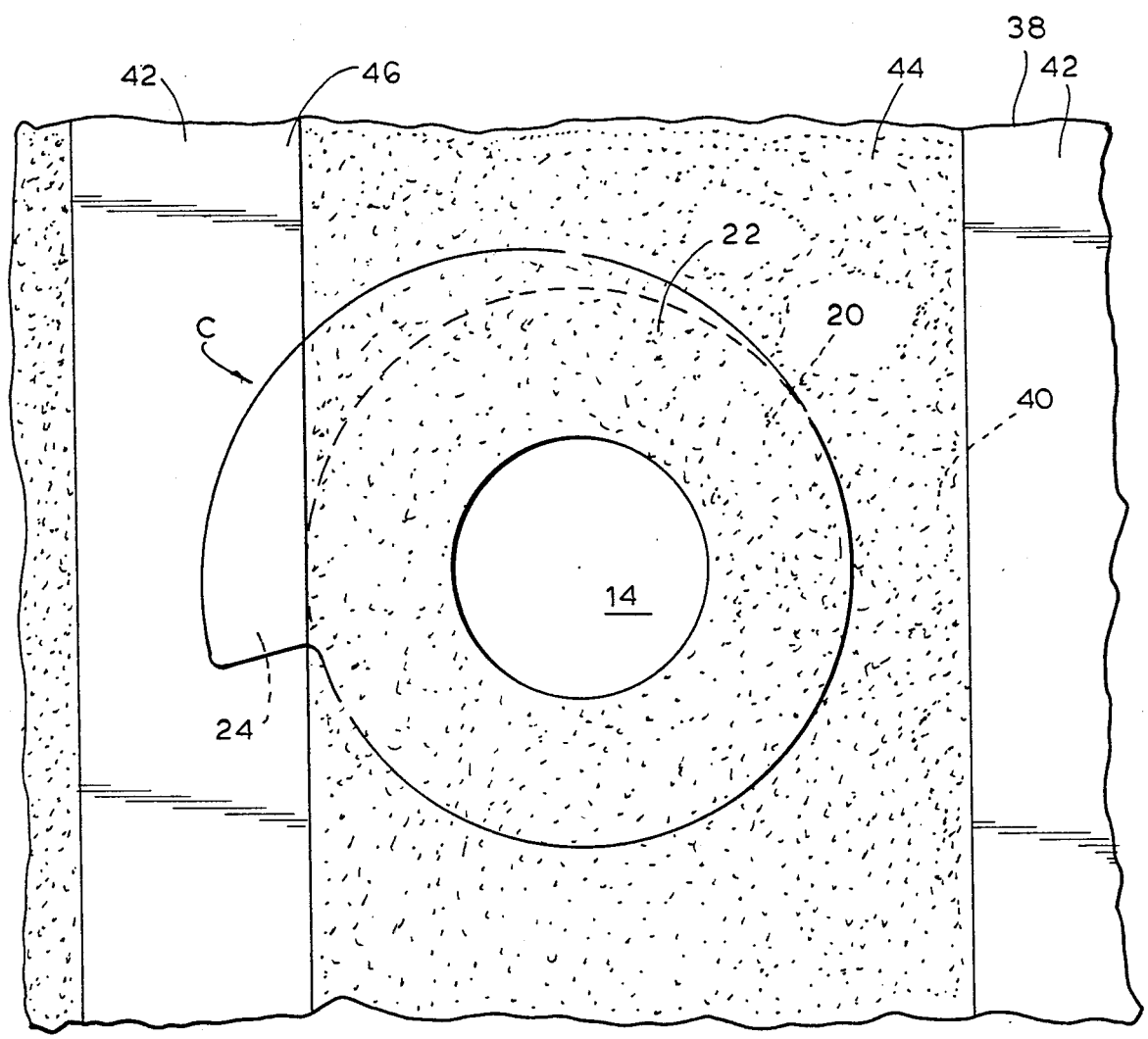
Figure 7:
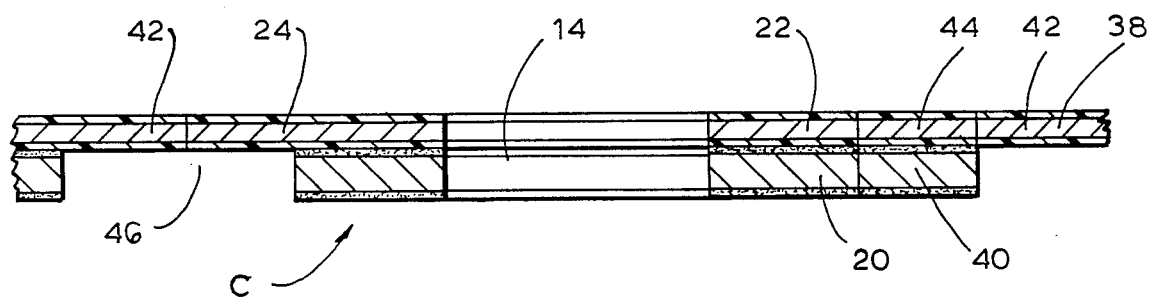
Figure 9:
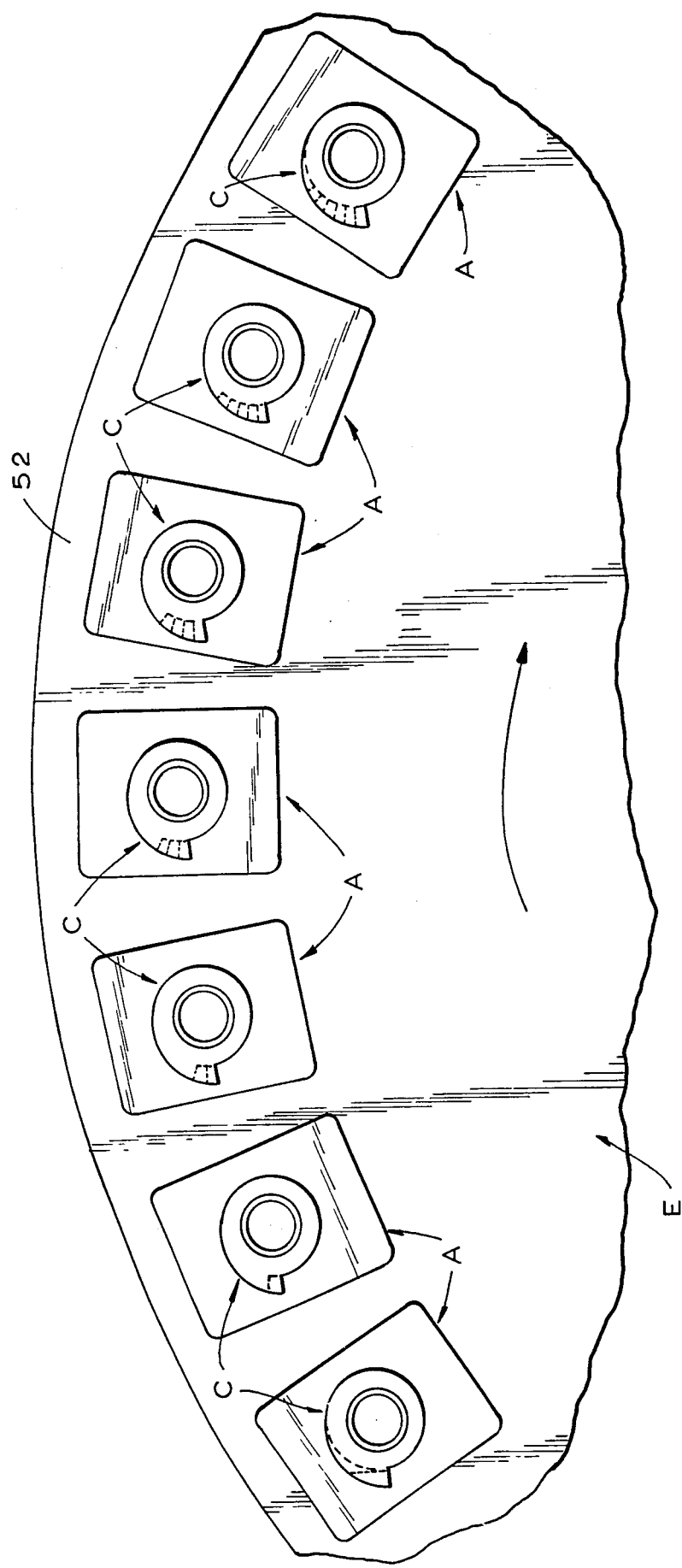

FIGS. 3A and 3B, taken together, are a top plan view of the apparatus of the present invention;

FIG. 4 is a side view of the apparatus of the present invention;

FIG. 5 is a view of a portion of the apparatus of the present invention taken along line 5—5 of FIG. 4;

FIG. 6 is a bottom view of a portion of the sheet from which the connecting parts are cut;

FIG. 7 is a cross-sectional view of a portion of the continuous sheet shown in FIG. 6;

FIG. 8 is a side view of a portion of the apparatus as seen along line 8-8 of FIG. 4; and, FIG. 9 is a top plan view of the operative portion of the rotatable table illustrated in FIGS. 3 and 4.

Figure 1:
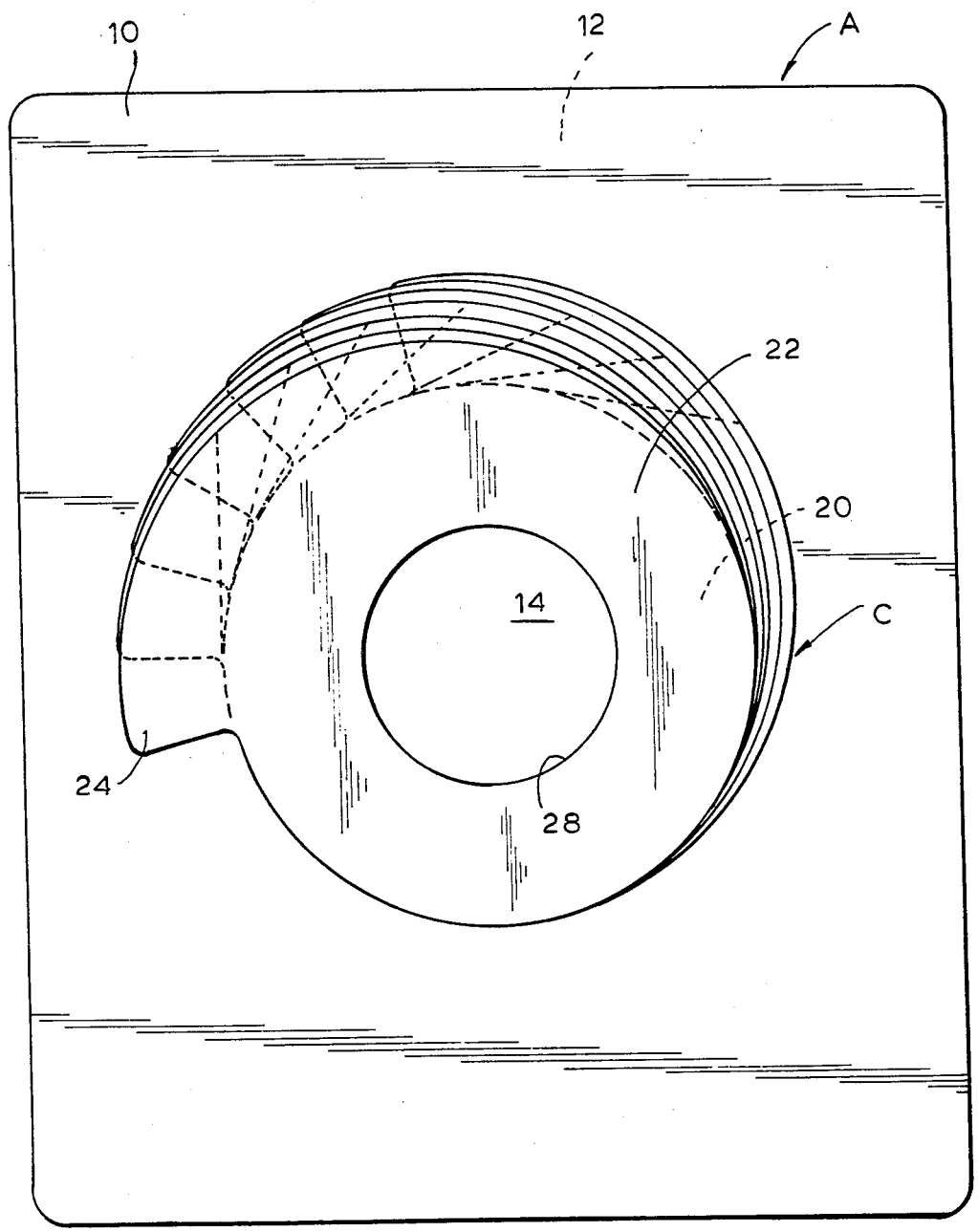
FIG. 1 is a front view of a faceplate with a stack of adhesive connecting rings mounted thereon in angularly offset relation.
Figure 2:
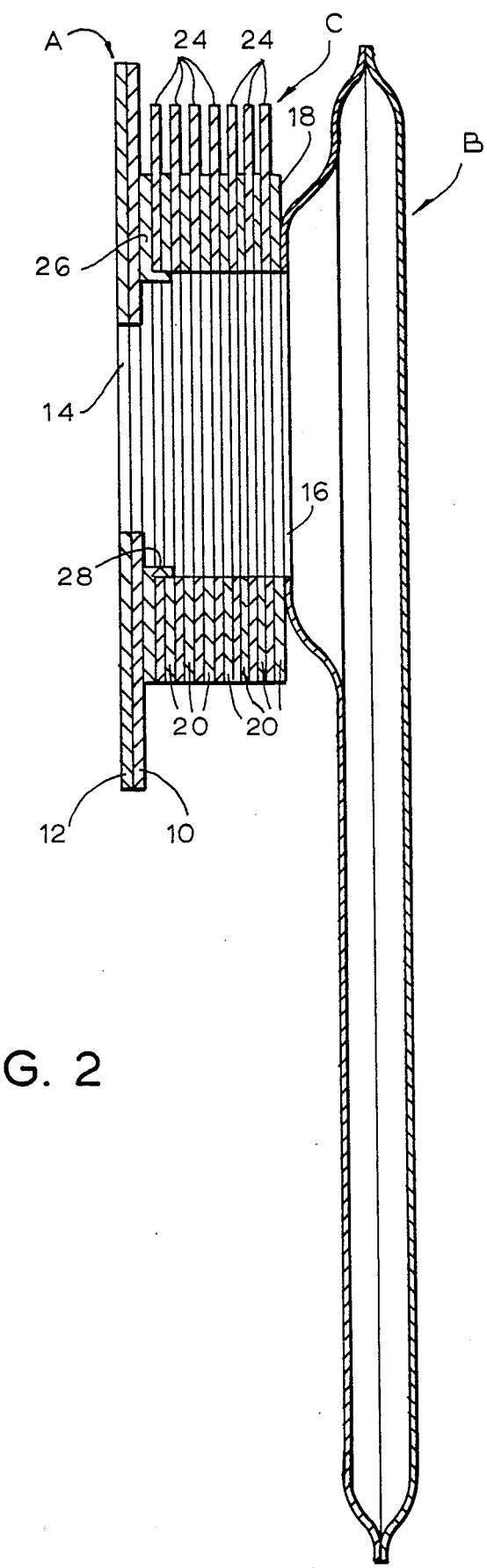
FIG. 2 is a side cross-sectional view of the faceplate shown in FIG. 1 with an ostomy pouch attached thereto.

The present invention relates to a method and apparatus for forming and mounting annular connecting parts or rings on a reusable ostomy appliance, such as is illustrated in FIGS. 1 and 2. As best seen in these figures, the ostomy appliance includes an adhesive-backed microporous pad, label or faceplate, formed of conventional materials, generally designated A. Faceplate A includes a flexible base layer 10, backed with a microporous adhesive layer 12. It is designed to be affixed to the skin surrounding the stoma. Faceplate A is provided with a central area 14 which can be cut to the appropriate size for receiving the stoma.

Connected to faceplate A is a flexible receiving pouch or bag, formed of conventional materials, generally designated B Pouch B is preferably made of thin plastic film or the like and is provided with an opening 16 in one side thereof. Surrounding opening 16 and permanently affixed to the exterior surface of the bag wall is a rigid or semi-rigid flange 18.

Pouch B is connected to faceplate A by a plurality of adhesive connecting rings, generally designated C. Each of the rings C includes a substantially annular base layer or carrier 20 coated with adhesive on both surfaces. Base layer 20 is provided with an overlying cover layer 22 so as to protect the adhesive on the top surface. Each layer 22 has a radially extending non-adhesive gripping portion 24 which functions to facilitate the gripping of the cover layer such that it can be conveniently peeled off from the base layer.

Rings C are mounted in vertical alignment in a stack upon a rigid or semi-rigid flange 26, permanently affixed to the surface of base 10 of faceplate A. Flange 26 is provided with an upstanding inner rim 28 so as to insure the proper alignment of the stack of connecting parts C. When the stoma receiving opening has been cut, faceplate A is affixed to the patient on the skin surrounding the stoma. The covering layer 22 of the topmost part C is then removed by gripping non-adhesive portion 24 between the fingers and peeling the cover layer from the annular base layer 20. The adhesive coating is then exposed and flange 18 on pouch B may be mounted on base layer 20 by pressing the flange against the exposed adhesive. A fluid-tight seal is achieved by uniform pressure around the flange 18. Pouch B can be removed when required for emptying or cleaning.

To remount the pouch, the used connecting ring C is removed. The radially extending nonadhesive portion 24 of the next ring C is grasped by the fingers and removed, exposing the fresh adhesive layer thereon. The pouch B can then be remounted. It should be noted that the topmost radially extending gripping portion 24 of cover layer 22 always obstructs access to the radially extending gripping portion 24 of the underlying base layers 20 such that only the topmost cover layer 22 can be removed.

Pouch B can be removed and reattached in this manner a number of times equal to the number of connecting rings C present in the stack. In the device illustrated in FIGS. 1 and 2, seven rings C are provided.

As is best seen in FIG. 1, the seven annular parts or rings C are annularly offset such that the gripping portions 24 are circumferentially spaced and, therefore, easily individually gripped in a manner which insures that only one ring at a time is peeled away. Moreover, only the gripping portion 24 of the topmost ring C is exposed. This prevents the inappropriate cover layer from being removed.

FIGS. 3-9 illustrate the apparatus for forming and mounting the adhesive connecting rings C on faceplates A. Referring to FIGS. 3 and 4, the apparatus comprises annular part or ring forming means, generally designated D, rotatable platform means, generally designated E, and part or ring distribution means, generally designated F.

Annular part forming means D forms spaced sets of parts or rings C on a continuous sheet. The part or ring sets are then transferred, in succession, into alignment with the rotatable platform means E. Once aligned with platform means E, means F removes the rings or parts C from the sheet and distributes the removed parts onto the platform. The rotatable platform E is indexed each time a set of parts is removed from the sheet and distributed on the platform. The parts in each set are formed in a pattern which coincides with the path of movement of the operative portion of the platform. Thus, the parts in each set may be distributed into respective stacks on the operative portion of the platform. By forming the parts in substantially the same orientation and rotating the platform in stepwise fashion before each set is distributed, the parts are mounted on each stack in the desired angularly offset relation.

Annular part forming means D includes a rotary die contour cutter in the form of roller 30 mounted on a shaft 32 intermittently driven in a conventional fashion, such as by a stepping motor. Roller 30 is provided with a plurality of die cutters 34, preferably five to seven (seven of which are shown). Die cutters 34 are located across roller 30 in an arcuate pattern which has a radius which is substantially equal to the distance between the center of rotatable platform means E and the operative portion thereof.

Cooperating with roller 30 is a second roller 36. A continuous sheet 38 of material extends between rollers 30 and 36. As illustrated in FIG. 7, sheet 38 consists of a non-adhesive layer 42 which will become cover layer 22. Layer 42 preferably comprises paper coated on each side with silicone. Different grades of silicone may be used for each side to permit sheet 38 to be rolled without sticking. Situated on layer 42 are seven spaced strips 44 each consisting of a base or carrier layer 40 of polyester, polyethylene or other suitable material. Layer 40 is adhesively coated on both sides. Annular base layers 20 will be formed from layer 40. The strips 44 are separated by portions 46 of non-adhesive layer 42.

As best seen in FIG. 3, dies 34 align with strips 44 of sheet 38 such that the annular sections of the dies are substantially entirely within the respective strips, whereas the radially extending portions thereof are aligned with the non-adhesive sections 46. Accordingly, the resulting parts C will include an annular part adhesively coated on both sides, having on one side a non-adhesive cover layer with a similar annular shape and a radially extending gripping portion.

As is conventional with rotary die cutting apparatus of the type herein described, each of the dies 34 is designed such that the part cut from sheet 38 is not entirely severed from the sheet. There exist several spaced lands or bridges (not shown) which maintain the connection between the part and the remainder of the sheet. The parts will remain in place on the sheet until they are removed, by severing the lands.

As will be readily appreciated from FIG. 3, the annular parts C are formed on sheet 38 in spaced sets of several parts (seven are illustrated) each. Parts C within each set are substantially identically oriented. In this case, the radially extending gripping portion 24 of each of the parts C extends to the left, as seen in FIG. 3. Sheet 38 is intermittently advanced towards rotatable platform E by the periodic rotation of drive shaft 32 and is supported in any suitable manner, such as by belts or chains (not shown) located on either edge of the sheet, having upstanding pins or the like to hold the sheet tacit. The belts or chains may be supported by powered sprockets to advance the sheet when required.

Faceplates A are brought to the edge of platform means E by a conveyor 50 or the like of conventional design. Conventional mechanical suction apparatus or the like may be provided to take each faceplate A, in turn, from conveyor 50 and place it on the upper surface of the platform means E. Alternatively, this operation can be done manually.

After each faceplate A is placed on platform means E, the platform is rotated through a given angle. Platform means E preferably comprises a substantially circular top 52 mounted on an upstanding shaft 53 driven by a conventional motor (not shown) which may be the same motor which rotates shaft 32 or be synchronized therewith. The motor connected to shaft 54 causes platform 52 to be indexeJ through a given angle each time it is actuated.

As the platform is indexed, the faceplates A thereon intermittently move towards an operative area which is in alignment with sheet 38. Faceplates A are spaced along the surface of platform 52 so as to coincide with the spacing between strips 44. At any one time, there are seven faceplates A located in the operative platform portion aligned with sheet 38. Each of these faceplates A is aligned with a different one of the respective parts C in the part set. Accordingly, when a part set is brought into alignment with the operative portion of platform 52, the seven faceplates A on the operative portion are respectively aligned with the parts C in the set.

Sheet 38 is held such that the leading set of parts C is immediately below means F. As shown in FIG. 8, means F consists of a plurality of vertically reciprocatable rods 54 mounted along an arcuate bracket 56 such that they can be raised and lowered in unison. Each of the rods 54 is provided with a vacuum actuated suction cup 58 of configuration similar to the annular parts C. As sheet 38 is held taut between means F and the operative portion of platform 52, bracket 56 is lowered such that the cups 58 of each of the rods 54 push the parts C to break the lands connecting the parts C with the remainder of sheet 38. The individual parts C adhere to cups 58 because of the suction which is operative. When rods 54 are at their lowermost positions, the suction is discontinued and the annular parts C are placed onto the faceplates A.

Bracket 56 is then moved upwardly, away from sheet 38 and sheet 38 is advanced towards the center of the platform so as to bring the next set of parts into alignment with the operative portion of platform 52. At the same time, platform 52 is indexed, rotating same through an angle, such that each of the faceplates on the platform is now positioned in the same position as the preceding faceplate A prior to the indexing. Distribution means F then operates on the next set of parts on sheet 38, causing same to be distributed on the respective faceplates A on the operative portion of platform 52. This sequence of operations is repeated continuously, seven parts being distributed on seven spaced faceplates each time platform 52 is indexed.

Referring back to FIG. 3, after faceplates A have passed through the operative portion of platform 52, they are indexed until they align with an exit conveyor 60 of conventional design. A mechanical suction take-off mechanism of any conventional design or the like, can be utilized to remove completed faceplates from platform 52 and place same on conveyor 60. Alternatively, this operation may be done manually.

FIG. 9 illustrates the operative portion of platform 52 having faceplates A thereon. The faceplates move from left to right, as seen in this figure, as platform 52 is rotated in a clockwise direction. The faceplate A in the first position (leftmost) on platform 52 has a single annular part C thereon. This is because it has been in the operative portion for one cycle of the operation. The second faceplate A (in the position to the right of the first faceplate) has two annular parts C mounted thereon because it has been in the operative portion of the platform for two cycles. Similarly, the third, fourth, fifth, sixth and seventh faceplates A, in sequence, have four, five, six and seven annular parts C mounted thereon, respectively, because they have been on the operative portion of the platform for four, five, six and seven cycles.

The annular parts C mounted on faceplates A are angularly off-set with respect to each other such that the non-adhesive gripping portions 24 are circumferentially spaced in a manner that permits same to be individually gripped. To insure that only the topmost cover layer is removed, the gripping portion thereof obscures the gripping portions of all of the other of the parts C. Stacking of parts C in angularly offset relation occurs because the parts are formed and distributed to the platform in identical orientations. However, faceplates A on the operative portion of the platform rotate through an angle each time platform 52 is rotated. The rotation of the faceplates through this angle causes each successive part to be stacked at a position which is angularly offset with respect to the previous part in the stack.

The amount of angular rotation between faceplate positions on platform 52 and, hence, gripping portions 24 of annular parts C, depends upon the geometry of the apparatus and the size of the faceplates. However, an angular offset in the range of 10° and 15° between each of the parts C is preferred as same is sufficient to provide the necessary separation between the consecutive gripping portions. In addition, it should be understood that while parts C are illustrated with radially extending portion 24 having a substantially arcuate configuration consisting of a relatively wide part gradually tapering to the circumference of the circular portion, other specific configurations may function with equal facility. For example, a generally rectangular or semicircular tab will function adequately.

It should now be appreciated that the present invention relates to a method and apparatus for forming adhesive connecting rings and stacking same on the faceplates of ostomy devices. The invention constitutes a highly automated manner of producing and mounting the parts in a high volume, low cost per unit operation which functions reliably.

While only a single preferred embodiment of the present invention has been disclosed herein for purposes of illustration, it is obvious that many variations and modifications could be made thereto. It is intended to cover all of these variations and modifications which fall within the scope of the present invention, as defined by the following claims:

I claim:

1. Apparatus for forming and stacking parts comprising means for forming sets of spaced parts by cutting the parts from a sheet of material in a substantially arcuate pattern, a platform, means for aligning successive ones of said sets with said platform by advancing said sheet towards said platform, means for rotating said platform to move a portion of said platform along a path substantially coincident with said arcuate pattern, means for distributing the parts from the successive aligned sets on said platform portion, so as to accumulate said parts in angularly offset relation in stacks, along said portion, as said platform is rotated.

2. The apparatus of claim 1, wherein said forming means comprises die cutting means.

3. The apparatus of claim 2, wherein said die cutting means comprises a rotary die contour cutting roller.

4. The apparatus of claim 1, wherein said cutting means has a plurality of dies distributed in a substantially arcuate pattern along the surface thereof.

5. The apparatus of claim 1, wherein said forming means partially cuts said parts from said sheet, and said distributing means comprises means for removing said parts from said sheet.

6. The apparatus of claim 1, wherein said parts are formed on said sheet and wherein said sets of parts are spaced along said sheet.

7. The apparatus of claim 1, wherein said parts are formed on said sheet and wherein said aligning means comprises means for intermittently advancing said sheet toward said platform.

8. The apparatus of claim 7, wherein said rotating means rotates said platform in a stepwise fashion.

9. The apparatus of claim 8, wherein said parts are formed on said sheet and wherein said aligning means advances said sheet toward said platform each time said moving means rotates said platform.

10. The apparatus of claim 1, wherein said rotating means rotates said platform in a stepwise fashion.

11. The apparatus of claim 1, further comprising means for feeding faceplates, one at a time, to said portion of said platform.

12. The apparatus of claim 11, further comprising means for removing faceplates from said portion of said platform after said portion has moved through said path.

13. The apparatus of claim 12, wherein said removing means comprises means for lifting said faceplate from said platform.

14. The apparatus of claim 1, wherein said parts have a substantially annular configuration.

15. The apparatus of claim 1, wherein said parts comprise a radially extending portion.

16. Apparatus for forming annular parts and stacking same comprising rotary means for cutting spaced sets of parts on a substantially continuous sheet, each of said sets comprising a plurality of spaced, substantially identically oriented parts, in a substantially arcuate pattern across said sheet, a substantially circular platform, means for advancing said sheet to bring said sets, one at a time, proximate said platform, means for rotating said platform in stepwise fashion, means for distributing said parts in said proximate set from said sheet onto said platform each time said platform is rotated, said parts accumulating in stacks on said platform, each of said stacks comprising parts in angularly offset relation.

17. The apparatus of claim 16, wherein said cutting means has a plurality of dies distributed in a substantially arcuate pattern along the surface thereof.

18. Apparatus for forming adhesive coated connecting rings and for stacking same on faceplates comprising means for cutting spaced sets of rings on a substantially continuous adhesive coated sheet, each of said sets comprising a plurality of spaced, substantially identically oriented rings, in a substantially arcuate pattern, a rotatable platform, means for intermittently advancing said sheet to bring said sets, one at a time, proximate said platform, means for feeding faceplates, one at a time, to the platform, means for indexing said platform to move said faceplates stepwise through a path substantially coincident with said arcuate pattern of said proximate set, means for removing said parts in said proximate set from said sheet each time said platform is indexed, placing said removed parts on said faceplates in angularly offset relation as said platform is moved, and means for removing said faceplates from said platform after same have moved through said path.

19. A method for forming and stacking parts on a platform comprising the steps of: forming sets of parts on a sheet of material in a substantially arcuate pattern, aligning successive sets of said parts with an operative portion of the platform by advancing the sheet toward the platform, rotating the platform to move the operative portion thereof along a path substantially coincident with the arcuate pattern, distributing successive aligned sets of parts on the operative portion of the platform, the parts accumulating in angularly offset relation in stacks along the operative portion, as the platform in rotated.

20. The method of claim 19, wherein the step of forming sets of parts comprises the step of die cutting the parts from said sheet of material.

21. The method of claim 20, wherein the step of distributing the parts comprises the steps of removing the parts from the sheet and releasing the parts onto the platform.

22. The method of claim 20, wherein the step of aligning comprises the step of intermittently advancing the sheet toward the platform.

23. The method of claim 19, wherein the step of rotating the platform comprises the step of rotating the platform in stepwise fashion.

24. The method of claim 19, further comprising the step of feeding faceplates, one at a time, to the platform.

25. A method for forming annular parts and stacking same on a substantially circular platform, the method comprising cutting spaced sets of parts on a substantially continuous sheet, each of the sets comprising a plurality of spaced, substantially identically oriented parts in a substantially arcuate pattern across the sheet, advancing the sheet towards the platform to bring the sets, one at a time, proximate the platform, rotating the platform in a stepwise fashion distributing the parts in the proximate set from the sheet on to the platform, each time the platform is rotated, the parts accumulating in stacks on the platform, as the platform is rotated, each of said stacks comprising parts in angularly offset relation.

26. The method of claim 25, further comprising the step of advancing the sheet each time the platform is rotated.

27. A method for forming adhesive coated connecting rings and for stacking same on faceplates on a platform comprising the steps of: cutting spaced sets of rings on a substantially continuous adhesive coated sheet, each of said sets comprising a plurality of spaced, substantially identically oriented rings in a substantially arcuate pattern, intermittently advancing the sheet toward the platform to bring the sets, one at a time, proximate the platform, indexing the platform to move the faceplates stepwise through a path substantially coincident with the arcuate pattern of the proximate set, removing the parts in the proximate set from the sheet, each time the platform is indexed, placing the removed parts on the faceplates in angularly offset relation as the platform is moved and removing the faceplates from the platform after same have moved through the path.

* * * * *